(12) United States Patent
Fjerdingstad (10) Patent No.: US 8,434,372 B2
(45) Date of Patent: May 7, 2013

(54) FLUID ANALYSIS SYSTEM AND METHOD FOR OPERATION OF AN ANALYSIS SYSTEM

(75) Inventor: Solve Fjerdingstad, Ås (NO)

(73) Assignee: Fras Technology AS, Ovre Ardal (NO)

( * ) Notice: Subject to any disclaimer, the term of this patent is extended or adjusted under 35 U.S.C. 154(b) by 163 days.

(21) Appl. No.: 13/063,261

(22) PCT Filed: Sep. 8, 2009

(86) PCT No.: PCT/NO2009/000314
§ 371 (c)(1),
(2), (4) Date: May 26, 2011

(87) PCT Pub. No.: WO2010/030189
PCT Pub. Date: Mar. 18, 2010

(65) Prior Publication Data
US 2011/0214511 A1     Sep. 8, 2011

(30) Foreign Application Priority Data
Sep. 12, 2008     (NO) .................................... 20083908

(51) Int. Cl.
*G01F 13/00*     (2006.01)
(52) U.S. Cl.
USPC ...................................................... 73/861.41
(58) Field of Classification Search ............... 73/861.41, 73/861.71, 61.43
See application file for complete search history.

(56) References Cited

U.S. PATENT DOCUMENTS
4,037,475 A     7/1977 Topham
4,091,653 A *  5/1978 Lee ................................ 73/1.28
(Continued)

FOREIGN PATENT DOCUMENTS
CN     101189409 A     5/2008
FR     2 653 554 A1     4/1991
(Continued)

OTHER PUBLICATIONS

Chinese Office Action for corresponding Chinese Patent Application No. 200980145641.3 mailed Aug. 28, 2012. English translation.
(Continued)

*Primary Examiner* — Jewel V Thompson
(74) *Attorney, Agent, or Firm* — Merchant & Gould P.C.

(57) ABSTRACT

A fluid analysis system is provided for analysis of a fluid flowing in a pipe or in a pipeline. The fluid analysis system comprises a pipe portion which, when the fluid analysis system is put to use, forms a part of the pipe or the pipeline through which the fluid flows. The pipe portion is provided with a fluid sample outlet for withdrawal of fluid samples from the fluid flowing through the pipe portion and a fluid sample return outlet for returning fluid samples to the pipe portion, where the fluid sample return outlet is arranged downstream of the fluid sample outlet. The fluid analysis system further comprises a fluid analyser which is provided in fluid communication with the fluid sample outlet and the fluid sample return outlet, and a propeller unit which is provided with at least one upstream propeller and at least one downstream propeller. The propeller unit is mounted in the pipe portion in such a manner that the upstream propeller is located upstream of the fluid sample outlet thereby enabling the upstream propeller to mix the fluid in the pipeline before fluid samples are withdrawn through the fluid sample outlet, and in such a manner that the downstream propeller is located downstream of the fluid sample outlet and upstream of the fluid sample return outlet.

21 Claims, 4 Drawing Sheets

U.S. PATENT DOCUMENTS

| | | | |
|---|---|---|---|
| 4,307,620 A | 12/1981 | Jiskoot | |
| 5,370,005 A * | 12/1994 | Fjerdingstad | 73/863.71 |
| 5,962,793 A * | 10/1999 | Payne | 73/861.41 |
| 7,461,547 B2 | 12/2008 | Terabayashi et al. | |
| 2004/0197922 A1 | 10/2004 | Cooper | |

FOREIGN PATENT DOCUMENTS

| | | |
|---|---|---|
| GB | 2 164 021 A | 3/1986 |
| JP | 2002-267510 A | 9/2002 |
| WO | WO 91/08467 A1 | 6/1991 |
| WO | WO 96/16325 A1 | 5/1996 |
| WO | WO 99/00656 A1 | 1/1999 |
| WO | WO 2004/057305 A2 | 7/2004 |
| WO | WO 2004/057306 A1 | 7/2004 |
| WO | WO 2008/111851 A1 | 9/2008 |
| WO | WO 2008/111851 A1 | 12/2008 |

OTHER PUBLICATIONS

International Search Report for corresponding International Patent Application No. PCT/NO2009/000314 mailed Jan. 28, 2010.

The Written Opinion of the International Searching Authority for corresponding International Patent No. PCT/NO2009/000314.

Norwegian Office Action for corresponding Norwegian Patent Application No. 20083908 mailed Mar. 6, 2009.

* cited by examiner

FLUID ANALYSIS SYSTEM AND METHOD FOR OPERATION OF AN ANALYSIS SYSTEM

This application is a National Stage Application of PCT/NO2009/000314, filed 8 Sep. 2009, which claims benefit of Serial No. 20083908, filed 12 Sep. 2008 in Norway and which applications are incorporated herein by reference. To the extent appropriate, a claim of priority is made to each of the above disclosed applications.

The present invention relates to a fluid analysis system for analysis of a fluid flowing in a pipe or in a pipeline. It is particularly applicable for a fluid analysis system arranged for counting particles in a fluid flowing in a pipe or a pipeline. The present invention further relates to a method for operation of a fluid analysis system for analysis of a fluid flowing in a pipe or a pipeline. The present invention also relates to use of the fluid analysis system.

The fluid analysis system is particularly useful for counting particles in a fluid flowing in a pipe or a pipeline located in areas with difficult access such as for example on an ocean or seabed. This may be in connection with control of hydraulic oil in hydraulic systems, for example in connection with equipment for production of hydrocarbons, where the equipment may be subsea production equipment. The invention is also particularly applicable in areas where there is a risk of explosion and/or fire.

From the American patent application U.S. 2004/0197922 A1 a system is known for detecting impurities in a water supply flowing in a pipe system. In the description it is also mentioned that a propeller may be provided in the pipe system for charging batteries which supply electricity for operation of the system.

A similar system is disclosed in the Japanese patent JP 2002267510, where electrical power required for operation of the system is provided by a battery which is charged by a propeller where the propeller is mounted in a pipe and driven by the fluid flow in the pipe.

The applicant's own patent application, WO 2004/057306 discloses in situ sampling and monitoring of a fluid by a fluid analyser which will be able to be used in connection with the invention in the present patent application. In U.S. Pat. No. 5,572,320 an analysis apparatus for determination of particulate material in fluid is described in detail.

When the number of particles present in a fluid has to be counted, the particles should be as uniformly distributed in the fluid as possible. Should the particles for some reason or other have a tendency to agglomerate in the fluid, it could give an entirely false picture of the particle density in the fluid if the fluid sample removed for counting particles either contains fluid with a particle density which is far below or far above the real particle density in the fluid. It is therefore advantageous to mix the fluid in order to obtain a uniform distribution of particles in the fluid before a fluid sample is removed for counting particles in the fluid.

Since the present system for particle counting is intended for use in environments with difficult access or where there is a risk of fire and/or explosion, it is also an advantage for the particle counter to be entirely or to the greatest possible extent self-sufficient in the energy required. This avoids the use of cables for supplying electrical energy for operating the particle counter. This applies, for example, to the light source for particle counting and image recognition, data processing, cable-free communication for transmitting data from the particle counter and/or control signals for controlling the particle counter and other parts of the system.

In other ways too it is an advantage if the whole system can function as far as possible without external intervention. An example of this is in avoiding the use of a pump for driving fluid samples through the fluid analysis system and possibly back to the pipe flow from which the fluid sample was removed.

The object of the present invention has therefore been to provide a fluid analysis system which attempts to solve the above-mentioned problems and which can therefore be employed in areas which are inaccessible or difficult to access, or in areas where there is a risk of fire and/or explosions.

This object is achieved with a fluid analysis system as defined in the independent claim 1, a method for operation of a fluid analysis system as defined in the independent claim 18, and by the use of the fluid analysis system as indicated in claims 20 and 21. Further preferred embodiments of the fluid analysis system are indicated in the associated dependent claims 2-17, while a further embodiment of the method for operation of the fluid analysis system is indicated in claim 19.

Thus a fluid analysis system is provided for analysis of a fluid flowing in a pipe or a pipeline. The fluid analysis system comprises a pipe portion, which, when the fluid analysis system is put to use, forms a part of the pipe or the pipeline through which the fluid flows. The pipe portion is provided with a fluid sample outlet for withdrawing fluid samples from the fluid flowing through the pipe portion and a fluid sample return outlet for returning fluid samples to the pipe portion where the fluid sample return outlet is arranged downstream of the fluid sample outlet. The fluid analysis system further comprises a fluid analyser which is arranged in fluid communication with the fluid sample outlet and the fluid return outlet and a propeller unit which is provided with at least one upstream propeller and at least one downstream propeller. The propeller unit is mounted in the pipe portion so that the upstream propeller is located upstream of the fluid sample outlet, thereby enabling the upstream propeller to mix the fluid in the pipeline before withdrawal of fluid samples through the fluid sample outlet, and in such a manner that the downstream propeller is located downstream of the fluid sample outlet and upstream of the fluid sample return outlet, thereby enabling the downstream propeller to provide a pressure drop in the pipe portion between the fluid sample outlet and the fluid sample return outlet which is sufficient to drive the fluid samples through the fluid analysis system.

The propeller unit further comprises a propeller housing in which is mounted at least one electrical generator. Normally one generator will be mounted in the propeller housing, but when, for example, a spare generator is required to take over the production of electricity in a situation where the generator which is normally in use has broken down or requires maintenance involving the need to stop the generator, more than one generator may be provided in the propeller housing.

The upstream and downstream propellers may be of traditional propeller design with a hub to which the blades are attached and with a propeller housing mounted in the pipe portion. The propeller housing is made as small as possible and as streamlined as possible in order to influence the pipe flow through the pipe portion to the least possible extent.

The diameter of the upstream propeller and the downstream propeller is chosen according to the function it has to perform. If the upstream propeller is arranged only for mixing the fluid in the pipe flow before the fluid sample outlet, the upstream propeller's blades will be able to be designed so as to create the degree of turbulence required for mixing the fluid. The desired degree of turbulence, and thereby the degree of mixing of the pipe flow may also be achieved by adapting the upstream propeller's diameter. The task of the downstream propeller is preferably to produce electrical energy and provide a pressure drop in the pipe portion between the fluid sample outlet and the fluid sample return outlet and the diameter may be chosen which best satisfies these two requirements.

As an alternative to an ordinary propeller design, the upstream propeller and/or the downstream propeller may be designed with a peripheral ring which is attached to the outer tips of the propeller blades in the radial direction, where the peripheral ring is rotatably mounted as a part of the pipe portion. The rotating ring can act as a rotor in an electrical generator, while the stator is mounted round the ring in the pipe portion. It is, of course, also possible to mount the peripheral ring on traditional bearings so that the propeller only rotates without producing electrical energy. This will be particularly relevant for the upstream propeller if it only has to mix the fluid in the pipe flow.

Another alternative will be a combination of these two types of propeller. In this case the downstream propeller is preferably provided with a peripheral ring and acts as the rotor in an electrical generator, while the upstream turbine is mounted on a shaft which is centrally attached to the downstream propeller and is substantially coaxial with the downstream propeller's axis of rotation. The shaft projects upstream from the downstream propeller so that the upstream propeller, which is mounted on the shaft, is located upstream of the fluid sample outlet. In order for the upstream propeller to be able to rotate, the upstream propeller is either rotatably mounted on the shaft which is fixed to the downstream propeller, or the upstream propeller is fixed to the shaft while the shaft is rotatably mounted in a hub in the centre of the downstream propeller (to which the downstream propeller's blades are then attached).

In addition to providing a pressure drop in the pipe portion, the downstream propeller will normally also drive, or help to drive, an electrical generator which is arranged in the propeller unit. Similarly, in addition to mixing the fluid in the pipeline, the upstream propeller can also drive, or help to drive, the electrical generator which is arranged in the propeller unit.

The fluid analysis system further comprises means for transmitting electrical energy from the at least one electrical generator to the fluid analyser and other power consumers in the fluid analysis system. These means will normally be ordinary electric cables which are freely available on the market.

In an embodiment of the invention the at least one upstream propeller and the at least one downstream propeller may be mounted on separate shafts, where the shafts are coaxial. The at least one upstream propeller and the at least one downstream propeller may be arranged in a contra-rotating manner. The electrical generator may then be a contra-rotating generator with the result that both the upstream propeller and the downstream propeller play a part in running the generator.

Another alternative is to mount the at least one upstream propeller and the at least one downstream propeller on the same shaft that drives the electrical generator.

Instead of mounting both the upstream propeller and the downstream propeller upstream of a propeller housing, the at least one upstream propeller may be mounted upstream of the propeller housing, and the at least one downstream propeller mounted downstream of the propeller housing. It is possible to mount the upstream propeller and the downstream propeller on a through-going shaft or they may be mounted on separate shafts which can then drive a contra-rotating generator.

In an embodiment of the invention the propeller unit comprises at least two electrical generators, where the at least one upstream propeller drives a first electrical generator and the at least one downstream propeller drives a second electrical generator.

The fluid analyser preferably comprises means for automatic counting of the number of particles in the fluid samples. These means may, for example, comprise a particle counter which is capable of identifying particles in a fluid sample and transmitting relevant data to a base station. In order to be able to store analysis data for the fluid samples, the fluid analysis system preferably comprises a data storage unit which can store data from the fluid analyser relating to each individual fluid sample.

The fluid analysis system further comprises means for transmitting data and/or control signals between the fluid analysis system and a base station at a distance from the fluid analysis system. The means for transmitting data and/or control signals may comprise one or more devices for wireless transmission of data and/or control signals between the fluid analyser and the base station. A mobile network and blue tooth are examples of wireless data transmission methods which may be employed.

The means for transmitting data and/or control signals may also comprise one or more cables for transmitting data and/or control signals between the fluid analyser and a base station if the fluid analyser is located in such a manner that this is expedient.

The fluid analyser preferably further comprises one or more sample containers for collecting one or more fluid samples, thereby enabling the number of particles in a fluid sample to be counted in a suitable laboratory. This may, for example, be relevant when automatic analysis of the fluid samples provides results which differ from anticipated values and have to be verified by means of a thorough analysis in a suitable laboratory. The sample container or sample containers are preferably releasably mounted in the fluid analyser in such a manner that the sample container can be removed from and placed in the fluid analyser by an ROV, a robot or similar equipment. This is particularly important when the system is used in areas which are difficult to access during normal operation.

The fluid analysis system preferably further comprises means for controlled withdrawal of a predetermined amount of fluid in a fluid sample. These means may be composed of one or more valve devices according to requirements. The valve devices are preferably automatic and advantageously designed so that they can be controlled from the base station.

Similarly the fluid analysis system preferably further comprises means which control the flow of fluid from fluid samples back to the pipe flow in the pipe portion and prevent fluid flow from the pipe portion through the fluid sample return outlet in the direction of the fluid analyser. These means may be composed of one or more valve devices. The valve devices are preferably automatic and advantageously capable of being controlled from the base station.

How great an amount should be removed from the fluid flow at any time through the pipe portion when a fluid sample is withdrawn may be regulated and set by means of the wireless system or the cables as mentioned above. Alternatively this may be regulated by setting the valve devices manually.

A method is also provided for operation of a fluid analyser for analysis of a fluid flowing in a pipe or a pipeline, where a fluid sample outlet is provided in the pipe or the pipeline. Through the fluid sample outlet a fluid sample is withdrawn which is passed to the fluid analyser for analysis of the fluid sample. The method comprises the following steps:

Providing a propeller unit comprising at least one upstream propeller and at least one downstream propeller, where the propellers are mounted on one or more rotating shafts and at an axial distance apart in the pipeline's longitudinal direction, and where at least one of the propellers is arranged to be able to drive an electrical generator mounted in the propeller unit.

Placing the propeller unit in the pipeline in such a manner that the at least one upstream propeller is located upstream of the fluid sample outlet in the pipeline and the at least one downstream propeller is located downstream of the fluid sample outlet.

In this manner the propellers provide mixing of the fluid before the fluid sample is withdrawn through the fluid sample outlet and production of electric current for operation of the fluid analyser and other equipment which requires electric current.

In an embodiment of the invention the method further comprises the step of placing the propeller unit in the pipeline in such a manner that the downstream propeller is located upstream of a fluid sample return outlet with which the pipeline is provided. In this manner a desired pressure drop can be provided in the pipeline between the fluid sample outlet and the fluid sample return outlet.

A use of a fluid analysis system is also provided for analysis of a fluid flowing in a pipe or a pipeline where the pipe portion forms a part of the pipe or the pipeline.

A use of a fluid analysis system is also provided for analysis of a fluid flowing in a pipe or a pipeline where the pipe or the pipeline is located under water, i.e. preferably on an ocean bed or seabed or in an environment where there is a risk of fire and/or explosion.

Some embodiments of the invention will now be described in greater detail with reference to the attached figures, in which

FIGS. 1-4 illustrate different embodiments of the invention. The different embodiments, however, have many common features which will be explained further before each individual embodiment is explained in more detail.

In the figures a fluid analysis system is illustrated which is generally indicated by the reference numeral 10. The fluid analysis system comprises a pipe portion 12, which, when the fluid analysis system 10 is in use, forms a part of a pipe or a pipeline. A pipe flow 50 of a fluid flows through the pipe or the pipeline. In some cases it will be desirable to carry out a regular check of the particle density in the fluid flow 50. This may, for example, be relevant for hydraulic systems where the number of particles and the size of the particles in the fluid flow 50 will be able to indicate to what extent there is evidence of wear and tear on the parts in the hydraulic system so that preventive maintenance can be initiated at an early point. Lubricating systems are another technical field in which the present invention will be able to be employed where the particle density in the lubricating fluid will be able to be used for detecting early signs of wear on various machine parts so that measures can be taken before a complete breakdown occurs of vital parts in the machine or machines which are being lubricated.

The pipe portion 12 is provided with a fluid sample outlet 35 and a fluid analyser 16. The fluid analyser 16 will preferably operate automatically and includes apparatus necessary for enabling an analysis of a fluid sample to be implemented. Amongst other things this includes a particle counter 17 where a fluid sample is examined. An example of such equipment is described in U.S. Pat. No. 5,572,320 as indicated in the introductory part of the application.

The automatic analysis equipment (not illustrated in detail in the figures) may for example include a laser diode which transmits light through the fluid sample. The light then passes from the laser through a magnifying lens before an image is registered on an image sensor chip. The image registered on the image sensor chip is then analysed by identification equipment which identifies and counts particles displayed on the image. In the process relevant data are preferably stored in a data storage medium 18 and transmitted, preferably wirelessly, to a base station 20 by means of communication equipment 19 comprising at least a transmitter and preferably a receiver. If the communication equipment 19 is provided with a receiver, the communication equipment can also be used for communication between the fluid analysis system 10 and the base station 20, which is normally located at a distance from the fluid analysis system 10, with the result that it is possible to control the fluid analysis system which, for example, may be located on the seabed.

The fluid analyser 16 is preferably connected to the pipe portion 12 by means of fluid lines 38, 39 and at least one valve device 43, which is preferably an automatic valve device, which controls withdrawal of fluid samples from the pipe flow 50 in the pipe portion 12 and the flow of the fluid samples through the fluid analyser.

After having passed through the fluid analyser 16, the fluid sample may be dumped in a store (not shown in the figures), or the fluid analyser 16 may be connected to a fluid sample return outlet 36 provided in the pipe portion 12, through fluid lines 40, 41, thus enabling the fluid sample to be returned to the fluid flow 50. The fluid sample return outlet 36 is preferably provided downstream of the fluid sample outlet 35 in the pipe portion 12. There is also provided at least one valve device 44, preferably an automatic valve device, in connection with the fluid lines 40, 41, thereby enabling the flow of fluid samples being returned to the pipe flow 50 in the pipe portion B12 to be regulated. By means of the at least one valve device 44 it is also possible to prevent fluid flow from the pipe flow 50 through the fluid lines 40, 41.

As already mentioned, the valve devices 43, 44 are preferably automatic, thereby enabling them to be controlled from the base station 20.

Data transmission and/or control of the fluid analysis system 10 is preferably conducted via a wireless system, but it may also be carried out by means of communication cables if the fluid analysis system 10 is located in such a manner that it is expedient and feasible to use communication cables.

The fluid analyser also preferably comprises a sample container (not illustrated in the figures) which can store a fluid sample withdrawn from the pipe portion 12. This sample container is preferably releasably mounted in the fluid analyser 17 in such a manner that it is removed by an ROV or other mechanical equipment and transported to a laboratory for detailed analysis. This may be relevant, for example, if results transmitted from the fluid analysis system provide grounds for undertaking a more thorough analysis of the fluid sample. The fluid analyser may, of course, also be provided with more than one sample container.

In the pipe portion 12 there is mounted a propeller unit 22. The propeller unit 22 comprises an upstream propeller 29, a downstream propeller 30 and at least one electrical generator 25, 26, 27 which is arranged in a propeller housing 23 and which is driven by one or both the propellers 29, 30. The propeller unit may be secured in position by means of fastening devices 24, such as e.g. stays or plates. The size of the propeller housing 23 is minimised and the propeller housing is designed so that the flow of fluid past the propeller housing is influenced to the least possible extent. The term upstream propeller here refers to the fact that the propeller is placed upstream of the fluid sample outlet 35, while downstream propeller correspondingly refers to the fact that the propeller is placed downstream of the fluid sample outlet 35. The exact distance upstream and downstream of the fluid sample outlet 35 at which the upstream propeller 29 and the downstream propeller 30 should be placed will depend amongst other things on the size (i.e. diameter) of the pipe and the propellers and what kind of fluid is flowing in the pipe portion. A person skilled in the art will be able to adapt the distances so as to achieve the object of the invention, possibly after a certain amount of testing if necessary.

Between the electrical generator 22 and the fluid analyser 16 and any other power consumers in the fluid analysis system, means are provided, preferably electric cables 28, for transmitting produced electric current. The electric current produced by the propeller unit 22 may be used to charge one or more batteries (not shown in the figures), which in turn supply the fluid analyser 16 and other power consumers in the fluid analysis system 10 with electric current.

In FIGS. 1-4 some examples are illustrated of how the upstream propeller and the downstream propeller may be arranged.

Figure 1:
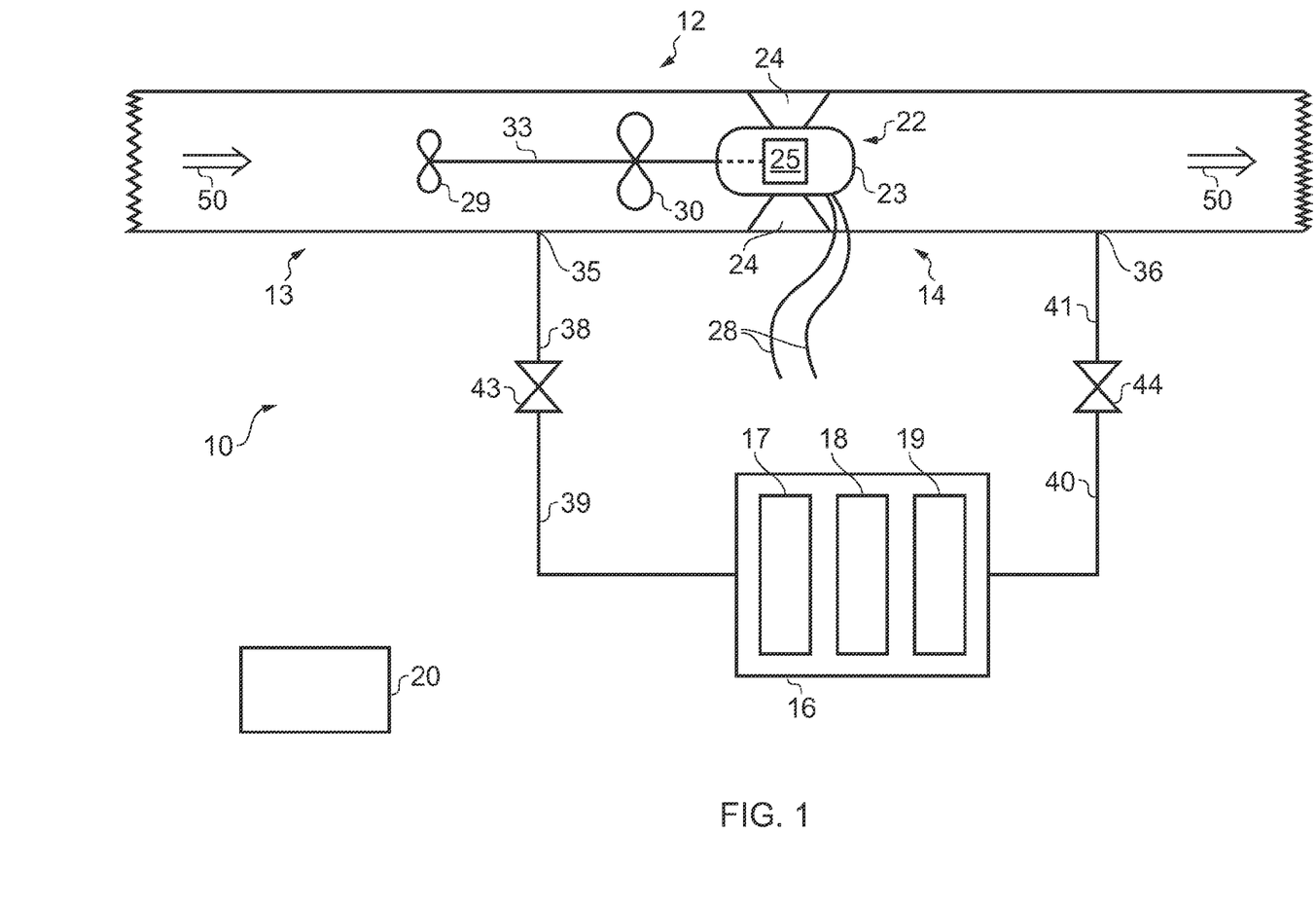
FIG. 1 is a schematic view of a first embodiment of the invention.

In FIG. 1 an embodiment of the invention is illustrated where the upstream propeller 29 and the downstream propeller 30 are mounted on a common shaft 33. The common shaft 33 drives the electrical generator 25 which is arranged in the propeller housing 23. The downstream propeller 30 may be designed in such a manner that it is this propeller which substantially helps to drive the electrical generator 25, while the upstream propeller 29 substantially helps to mix the fluid in the fluid flow 50 at the front edge of the fluid sample outlet 35. The design and setting of the blades on the upstream propeller 29 will be decisive for the extent to which the fluid in the fluid flow 50 is mixed. This applies to all the different embodiments of the present invention. The downstream propeller 30 will also preferably provide the required pressure drop in the pipe portion 12 between the fluid sample outlet 35 and the fluid sample return outlet 36, thereby causing the fluid samples to be driven through the fluid analyser and back to the pipe flow 50 without the need for any kind of pump arrangement.

Figure 2:
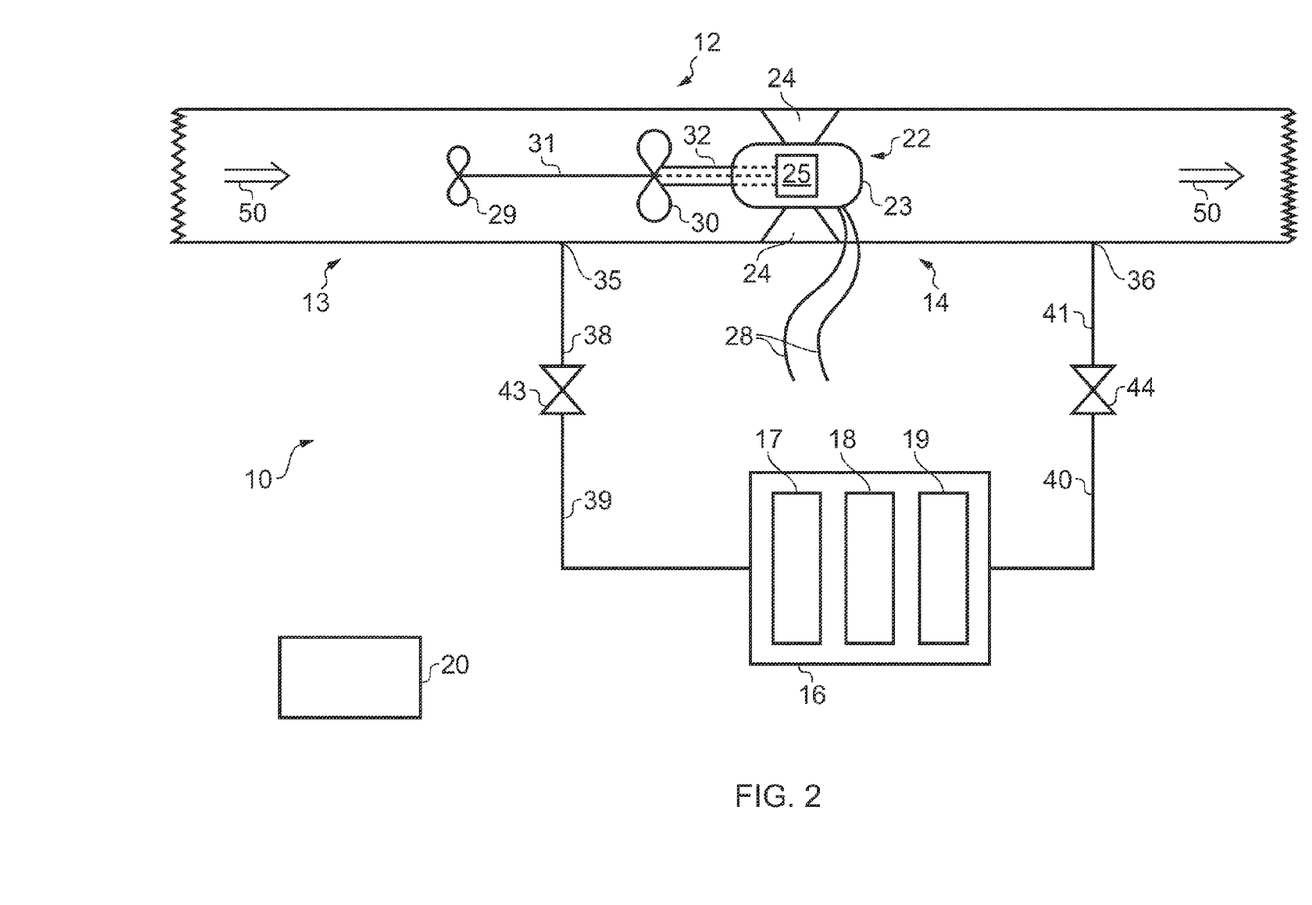
FIG. 2 is a schematic view of a second embodiment of the invention.

In FIG. 2 an embodiment of the invention is illustrated where the upstream propeller 29 is mounted on an upstream propeller shaft 31 while the downstream propeller 30 is mounted on a downstream propeller shaft 32 where the upstream propeller shaft 31 and the downstream propeller shaft 32 are coaxially mounted. There are substantially two possibilities for operation of the electrical generator 25 for this embodiment. The downstream propeller 30 can drive the electrical generator 25, while the upstream propeller 29 is mounted in such a way that it rotates independently of the downstream propeller's rotation and only contributes to mixing of the fluid, for example by the upstream propeller shaft 31 being rotatably mounted inside the downstream propeller shaft 32 which may be cylindrical in shape. Alternatively, the upstream propeller 29 and the downstream propeller 30 may be mounted in such a way that they are contra-rotating and both help to drive the electrical generator and thereby the production of electricity. Contra-rotating generators are known in the prior art and will not be described further here. The downstream propeller 30 will also preferably provide the required pressure drop in the pipe portion 12 between the fluid sample outlet 35 and the fluid sample return outlet 36, thereby causing the fluid samples to be driven through the fluid analyser and back to the pipe flow 50 without the need to use any kind of pump arrangement.

Figure 3:
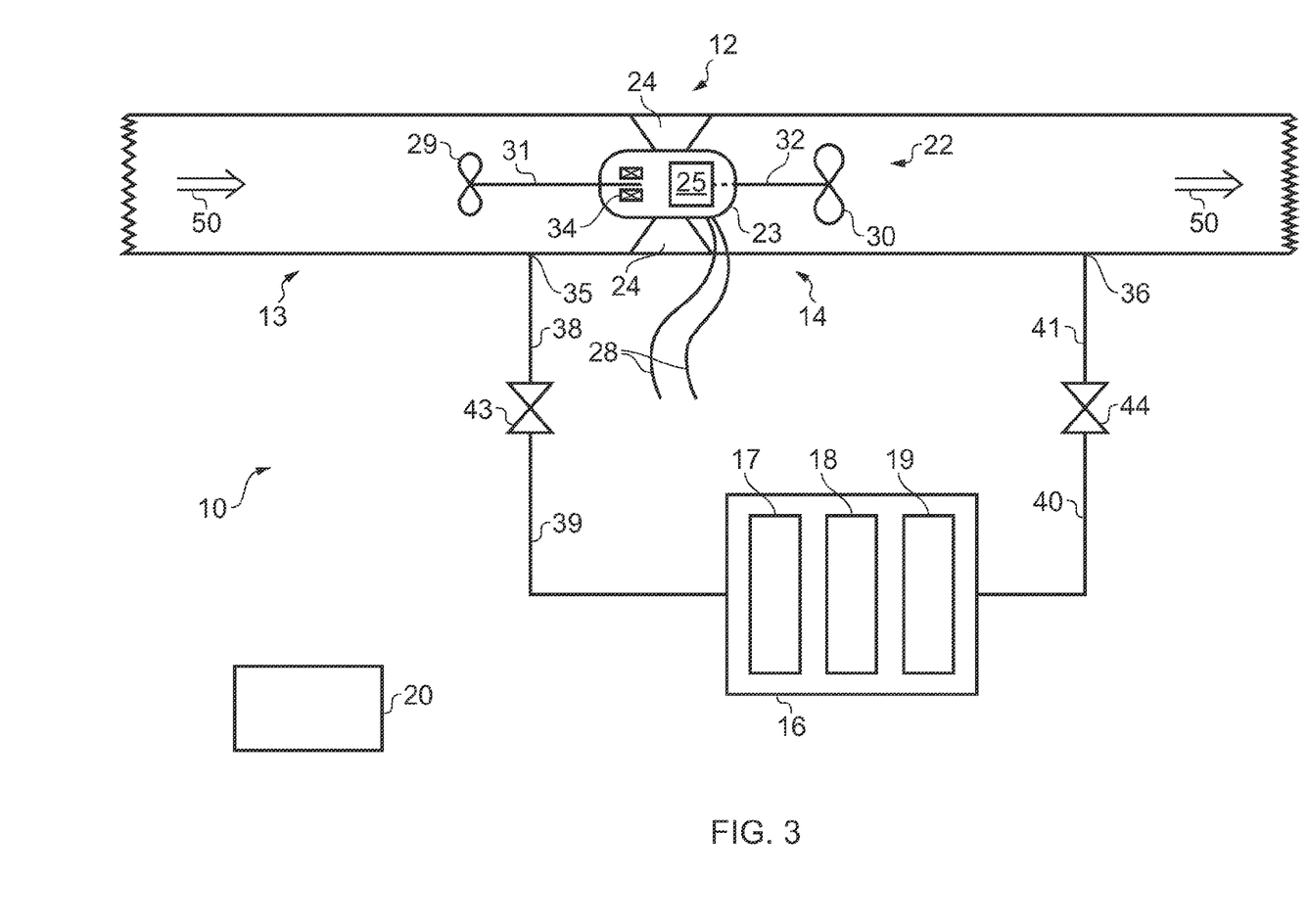
FIG. 3 is a schematic view of a third embodiment of the invention.

In FIG. 3 an embodiment of the invention is illustrated where the upstream propeller 29 and the downstream propeller 30 are mounted on each side of the propeller housing 23. The upstream propeller 29 is mounted upstream of the propeller housing 23 and the fluid sample outlet 35, while the downstream propeller 30 is mounted downstream of the fluid sample outlet 35 and upstream of the fluid sample return outlet 36. In the figure an embodiment is illustrated where the upstream propeller 29 is mounted by means of bearings 34 and rotates independently of the downstream propeller 30 and the electrical generator 25. The electrical generator is therefore driven only by the downstream propeller 30. An alternative will of course be to mount the upstream propeller 29 and the downstream propeller 30 on a through-going common shaft where both the propellers 29, 30 help to drive the electrical generator 25. The downstream propeller 30 will also preferably provide the required pressure drop in the pipe portion 12 between the fluid sample outlet 35 and the fluid sample return outlet 36, thereby causing the fluid samples to be driven through the fluid analyser and back to the pipe flow 50 without the need to use any kind of pump arrangement.

Figure 4:
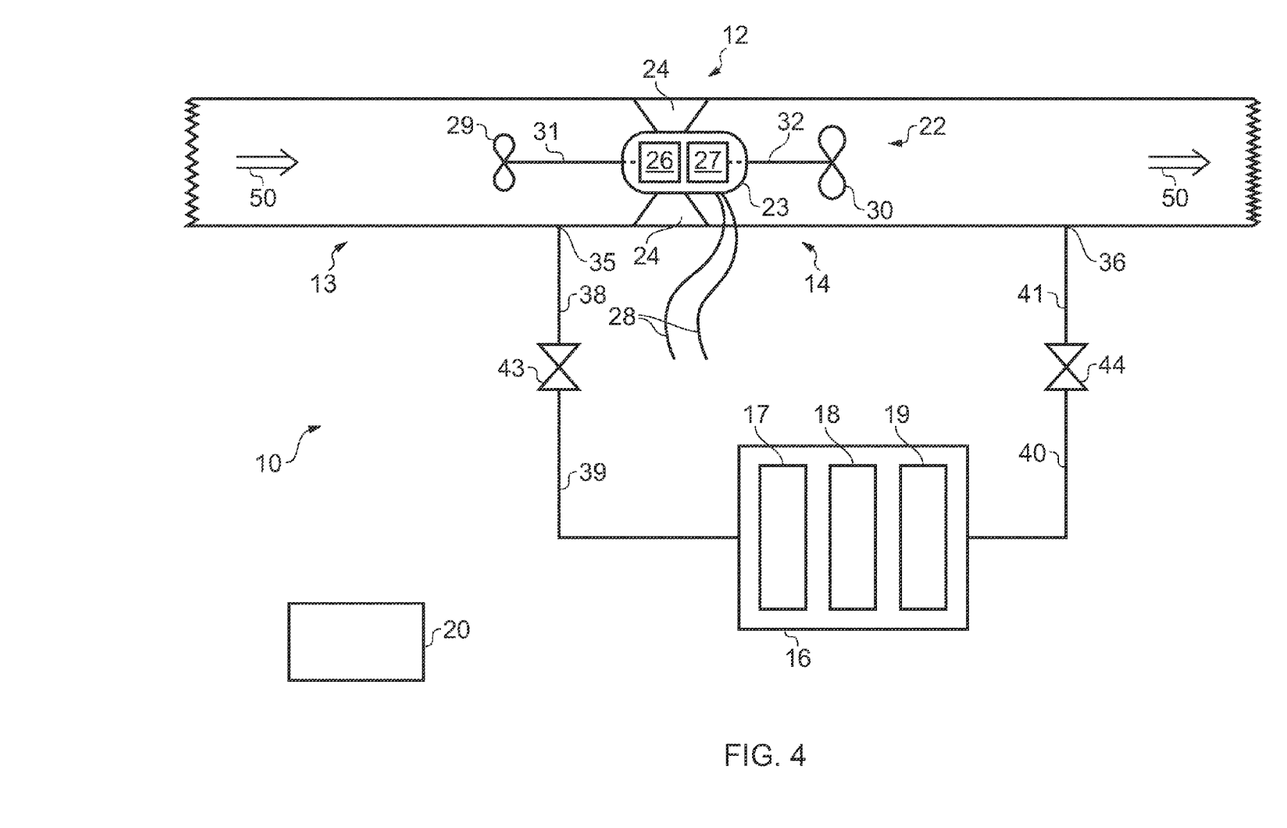
FIG. 4 is a schematic view of a fourth embodiment of the invention.

In FIG. 4 an embodiment of the invention is illustrated where the upstream propeller 29 and the downstream propeller 30 are mounted on each side of the propeller housing 23 in a similar manner to that illustrated in FIG. 3. The upstream propeller 29 is mounted upstream of the propeller housing 23 and the fluid sample outlet 35, while the downstream propeller 30 is mounted downstream of the fluid sample outlet 35 and upstream of the fluid sample return outlet 36. The propeller unit 22, however, is provided with a first electrical generator 26 and a second electrical generator 27, both of which are disposed in the propeller housing 23. The upstream propeller 29 drives the first electrical generator 26 via the upstream propeller shaft 31, while the downstream propeller 30 drives the second electrical generator 27 via the downstream propeller shaft 32. During normal operation one of the two electrical generators 26, 27 will be able to be disconnected so that only one generator is in operation and producing electrical energy. The first generator 26, which is driven by the upstream propeller 29, will preferably be disengaged during normal operation. The downstream propeller 30 will then drive the second generator 27 while simultaneously providing a pressure drop between the fluid sample outlet 35 and the fluid sample return outlet 36, while the upstream propeller just mixes the fluid in the fluid flow 50 during normal operation. In the event of necessary maintenance or breakdown of the second electrical generator 27, the first generator 26 will be able to be switched on, thereby permitting the production of electricity to continue.

A number of embodiments of the invention have now been described, which mixes the fluid in the fluid flow 50 before fluid samples are removed from the fluid flow and which will make the fluid analysis system 10 independent of the external supply of electrical power and use of a pump for pumping fluid samples through the fluid analysis system 10 and back to the pipe portion 12.

The system described above may of course be used anywhere, but it is particularly suitable for use in areas with difficult access, such as for example in connection with bottom-based installations for production of hydrocarbons at sea. It is also well-suited for use in areas where there is an environment with a risk of fire and explosion.

The invention claimed is:

1. A fluid analysis system for analysis of a fluid in a pipe flow flowing in a pipe or in a pipeline, which fluid analysis system comprises
a pipe portion which, when the fluid analysis system is put to use, forms a part of the pipe or the pipeline through which the fluid flows, which pipe portion is provided with a fluid sample outlet for withdrawal of fluid samples from the pipe flow in the pipe portion and a fluid sample return outlet for returning fluid samples to the pipe flow in the pipe portion, which fluid sample return outlet is arranged downstream of the fluid sample outlet;
a fluid analyser which is provided in fluid communication with the fluid sample outlet and the fluid sample return outlet,
wherein the fluid analysis system further comprises a propeller unit which is provided with at least one upstream propeller and at least one downstream propeller, which propeller unit is mounted in the pipe portion in such a manner that
the upstream propeller is located upstream of the fluid sample outlet, thereby enabling the upstream propeller to mix the pipe flow in the pipe portion before fluid samples are withdrawn through the fluid sample outlet,
the downstream propeller is located downstream of the fluid sample outlet and upstream of the fluid sample return outlet, thereby enabling the downstream propeller to provide a pressure drop in the pipe portion between the fluid sample outlet and the fluid sample return outlet which is sufficient to drive the fluid samples through the fluid analysis system.

2. A fluid analysis system according to claim 1, wherein the propeller unit comprises a propeller housing in which at least one electrical generator is provided.

3. A fluid analysis system according to claim 2, wherein in addition to providing a pressure drop in the pipe portion, the downstream propeller also drives, or helps to drive, the electrical generator which is arranged in the propeller housing.

4. A fluid analysis system according to claim 2, wherein in addition to mixing the pipe flow in the pipe portion, the upstream propeller also drives, or helps to drive, the electrical generator which is arranged in the propeller housing.

5. A fluid analysis system according to claim 2, wherein the fluid analysis system comprises means for transmitting electrical energy from the electrical generator to the fluid analyser and other power consumers in the fluid analysis system.

6. A fluid analysis system according to claim 1, wherein the at least one upstream propeller and the at least one downstream propeller are mounted on separate shafts, which shafts are coaxial.

7. A fluid analysis system according to claim 6, wherein the at least one upstream propeller and the at least one downstream propeller are mounted in a contra-rotating manner.

8. A fluid analysis system according to claim 1, wherein that the at least one upstream propeller and the at least one downstream propeller are mounted on the same shaft.

9. A fluid analysis system according to claim 2, wherein the at least one upstream propeller is mounted upstream of the propeller housing and the at least one downstream propeller is mounted downstream of the propeller housing.

10. A fluid analysis system according to claim 1, wherein the propeller unit comprises two electrical generators, where the at least one upstream propeller drives a first electrical generator and the at least one downstream propeller drives a second electrical generator.

11. A fluid analysis system according to claim 1, wherein the fluid analyser comprises a particle counter for automatic counting of the number of particles in the fluid samples.

12. A fluid analysis system according to claim 11, wherein the fluid analyser comprises a data storage unit which can store data from the particle counter relating to each individual fluid sample.

13. A fluid analysis system according to claim 1, wherein the fluid analysis system comprises means for transmitting data and/or control signals between the fluid analysis system and a base station located at a distance from the fluid analysis system.

14. A fluid analysis system according to claim 13, wherein the means for transmitting data and/or control signals comprises one or more devices for wireless transmission of data and/or control signals between the fluid analyser and the base station.

15. A fluid analysis system according to claim 13, wherein the means for transmitting data and/or control signals comprises one or more cables for transmitting data and/or control signals between the fluid analyser and the base station.

16. A fluid analysis system according to claim 1, wherein the fluid analyser comprises a sample container for collecting a fluid sample, thereby enabling the number of particles in the fluid sample to be counted in a suitable laboratory.

17. A fluid analysis system according to claim 16, wherein the sample container is releasably mounted in the fluid analyser in such a manner that the sample container can be removed from and placed in the fluid analyser by an ROV, a robot or similar equipment.

18. A method for operation of a fluid analyser for analysis of a fluid in a pipe flow flowing in a pipe or a pipeline, where there is provided in the pipe or the pipeline a fluid sample outlet, through which a fluid sample is withdrawn which is passed to the fluid analyser for analysis of the fluid sample, wherein the method comprises the following steps:
providing a propeller unit comprising at least one upstream propeller and at least one downstream propeller, which propellers are mounted on one or more rotating shafts and at an axial distance apart in the pipeline's longitudinal direction, and where at least one of the propellers is arranged to be able to drive one or more electrical generators arranged in the propeller unit,
placing the propeller unit in the pipeline in such a manner that the at least one upstream propeller is located upstream of the fluid sample outlet in the pipeline and the at least one downstream propeller is located downstream of the fluid sample outlet,
whereby the propellers provide mixing of the fluid in the pipe flow before the fluid sample is withdrawn through the fluid sample outlet and production of electric current for operation of the fluid analyser and other power-consuming equipment.

19. A method according to claim 18, wherein the propeller unit is furthermore placed in the pipeline in such a manner that the downstream propeller is located upstream of a fluid sample return outlet with which the pipeline is provided, whereby a desired pressure drop can be provided in the pipeline between the fluid sample outlet and the fluid sample return outlet.

20. The use of a fluid analysis system according to claim 1 for analysis of a fluid in a pipe flow flowing in a pipe portion where the pipe portion forms a part of a pipe or a pipeline.

21. The use of a fluid analysis system according to claim 1 for analysis of a fluid in a pipe flow flowing in a pipe portion where the pipe portion forms a part of a pipe or a pipeline which is located under water or in an environment where there is a risk of fire and/or explosion.

* * * * *